US011363814B2

(12) United States Patent
Toebes

(10) Patent No.: US 11,363,814 B2
(45) Date of Patent: *Jun. 21, 2022

(54) ANTI-BACTERIAL COMPOSITIONS

(71) Applicant: Biocidium IP Holdco, Co., North Vancouver (CA)

(72) Inventor: Jan Willem Toebes, Abbotsford (CA)

(73) Assignee: Biocidium IP Holdco, Co.

( * ) Notice: Subject to any disclaimer, the term of this patent is extended or adjusted under 35 U.S.C. 154(b) by 0 days.

This patent is subject to a terminal disclaimer.

(21) Appl. No.: 16/931,376

(22) Filed: Jul. 16, 2020

(65) Prior Publication Data

US 2021/0037820 A1 Feb. 11, 2021

Related U.S. Application Data

(63) Continuation of application No. 15/545,863, filed as application No. PCT/CA2016/050055 on Jan. 22, 2016, now Pat. No. 10,716,305.

(60) Provisional application No. 62/106,816, filed on Jan. 23, 2015.

(51) Int. Cl.

| | |
|---|---|
| *A01N 33/08* | (2006.01) |
| *A01N 37/06* | (2006.01) |
| *A01N 37/36* | (2006.01) |
| *A61K 8/365* | (2006.01) |
| *A61K 8/41* | (2006.01) |
| *A61K 31/133* | (2006.01) |
| *A61K 31/19* | (2006.01) |
| *A61K 31/201* | (2006.01) |
| *A61K 8/36* | (2006.01) |
| *A61Q 17/00* | (2006.01) |
| *A61K 45/06* | (2006.01) |

(52) U.S. Cl.
CPC ............ *A01N 33/08* (2013.01); *A01N 37/06* (2013.01); *A01N 37/36* (2013.01); *A61K 8/361* (2013.01); *A61K 8/365* (2013.01); *A61K 8/41* (2013.01); *A61K 31/133* (2013.01); *A61K 31/19* (2013.01); *A61K 31/201* (2013.01); *A61K 45/06* (2013.01); *A61Q 17/005* (2013.01)

(58) Field of Classification Search
CPC ...... A61K 45/06; A61K 31/133; A61K 8/365; A61K 31/201; A61K 31/19; A61K 8/41; A61K 8/361; A61K 2300/00; A01N 37/36; A01N 33/08; A01N 37/06; A61Q 17/005

See application file for complete search history.

(56) References Cited

U.S. PATENT DOCUMENTS

| | | |
|---|---|---|
| 5,011,472 A | 4/1991 | Aebischer et al. |
| 5,023,252 A | 6/1991 | Hseih |
| 5,648,389 A | 7/1997 | Gans et al. |
| 7,645,803 B2 | 1/2010 | Tamarkin et al. |
| 7,704,518 B2 | 4/2010 | Tamarkin et al. |
| 7,727,568 B2 | 6/2010 | Cazemier |
| 7,851,424 B2 | 12/2010 | Barnhart et al. |
| 8,372,790 B2 | 2/2013 | Barnhart et al. |
| 8,795,693 B2 | 8/2014 | Tamarkin et al. |
| 8,852,648 B2 | 10/2014 | Salamone et al. |
| 8,865,201 B2 | 10/2014 | De Luigi Bruschi et al. |
| 10,716,305 B2 * | 7/2020 | Toebes ............... A61K 8/41 |
| 2002/0041901 A1 | 4/2002 | Murad |
| 2002/0172719 A1 | 11/2002 | Murad |
| 2003/0019813 A1 | 1/2003 | Ottersbach et al. |
| 2005/0019461 A1 | 1/2005 | Cazemier |
| 2005/0271595 A1 | 12/2005 | Brown |
| 2006/0034902 A1 | 2/2006 | Cormier et al. |
| 2006/0275218 A1 | 12/2006 | Tamarkin et al. |
| 2006/0275221 A1 | 12/2006 | Tamarkin et al. |
| 2008/0026974 A1 | 1/2008 | Barnhart et al. |
| 2008/0045491 A1 | 2/2008 | Fitchmun |
| 2008/0206159 A1 | 8/2008 | Tamarkin et al. |
| 2008/0207774 A1 | 8/2008 | Krishnan |
| 2008/0226760 A1 | 9/2008 | Torrent Campmany |
| 2008/0233062 A1 | 9/2008 | Krishnan |

(Continued)

FOREIGN PATENT DOCUMENTS

| | | |
|---|---|---|
| AU | 2007203322 B2 | 2/2008 |
| CA | 2320541 A1 | 3/2001 |

(Continued)

OTHER PUBLICATIONS

First Office Action for corresponding Chinese application No. 201680016649.X; dated Dec. 17, 2019 (8 pages).
Communication pursuant to Article 94(3) EPC for corresponding European application No. 16739714.0; dated Dec. 16, 2019 (7 pages).
Examination Report for corresponding Indian application No. 201717029842; dated Oct. 18, 2019 (5 pages).

(Continued)

*Primary Examiner* — Blessing M Fubara
(74) *Attorney, Agent, or Firm* — Mendelsohn Dunleavy, P.C.

(57) ABSTRACT

According to one embodiment, a method of managing messages in a trading network is provided. A set of user relationships between a first user and one or more second users authorized to act on behalf of the first user is stored. A trading message regarding a trading order submitted on behalf of the first user is received from a trading system. The trading message is communicated to the first user. Each of the second users is identifying from the set of user relationships. For each of the identified second users, a carrier message is generated that includes the trading message and routing information associated with that second user. For each of the identified second users, the respective carrier message is communicated toward a user application associated with that second user based at least on the routing information included in the respective carrier message.

27 Claims, No Drawings

(56) References Cited

U.S. PATENT DOCUMENTS

| | | |
|---|---|---|
| 2009/0209443 A1 | 8/2009 | Barnhart et al. |
| 2010/0056628 A1 | 3/2010 | Stockel et al. |
| 2010/0111879 A1 | 5/2010 | Tamarkin et al. |
| 2011/0033402 A1 | 2/2011 | Modi |
| 2011/0263471 A1 | 10/2011 | Barnhart et al. |
| 2012/0289591 A1 | 11/2012 | Folan |
| 2014/0127320 A1 | 5/2014 | Salamone et al. |
| 2015/0017103 A1 | 1/2015 | Tamarkin et al. |

FOREIGN PATENT DOCUMENTS

| | | |
|---|---|---|
| CA | 2594270 A1 | 1/2008 |
| CA | 2584270 C | 7/2013 |
| CN | 101035589 A | 9/2007 |
| CN | 102056997 A | 5/2011 |
| CN | 102159181 A | 8/2011 |
| CN | 101861175 A | 6/2013 |
| CN | 103357015 A | 10/2013 |
| CN | 102639129 B | 8/2016 |
| EP | 0252276 B1 | 8/1992 |
| EP | 1886660 A1 | 2/2008 |
| GB | 1194863 A | 6/1970 |
| GB | 2414666 A | 12/2005 |
| JP | S62298517 A | 12/1987 |
| JP | H10158161 A | 6/1998 |
| JP | 2008056912 A | 3/2008 |
| JP | 2011522069 A | 7/2011 |
| RU | 2010149884 A | 6/2012 |
| RU | 2010149893 A | 6/2012 |
| WO | WO9602563 A1 | 2/1996 |
| WO | WO9715282 A1 | 5/1997 |
| WO | WO9951218 A1 | 10/1999 |
| WO | WO0038617 A2 | 7/2000 |
| WO | WO0128552 A2 | 4/2001 |
| WO | WO2006020842 A1 | 2/2006 |
| WO | WO2006085907 A2 | 8/2006 |
| WO | WO2007039825 A2 | 4/2007 |
| WO | WO2007054818 A2 | 5/2007 |
| WO | WO2008021441 A2 | 2/2008 |
| WO | WO2008152444 A2 | 12/2008 |
| WO | WO2009019477 A2 | 2/2009 |
| WO | WO2009137014 A1 | 11/2009 |
| WO | WO2009140062 A1 | 11/2009 |
| WO | WO2010019180 A1 | 2/2010 |
| WO | WO2011061237 A1 | 5/2011 |
| WO | WO2013112548 A1 | 8/2013 |
| WO | WO2013149323 A1 | 10/2013 |
| WO | WO2014035246 A1 | 3/2014 |
| WO | WO2014074289 A1 | 5/2014 |
| WO | WO2014195872 A1 | 12/2014 |
| WO | WO2016115639 A1 | 7/2016 |

OTHER PUBLICATIONS

Bergsson, Gudmundur, et al. "In vitro killing of Candida albicans by fatty acids and monoglycerides." Antimicrobial agents and chemotherapy 45.11 (2001): 3209-3212.
Diekema, D. J., et al. "Survey of infections due to *Staphylococcus* species: frequency of occurrence and antimicrobial susceptibility of isolates collected in the United States, Canada, Latin America, Europe, and the Western Pacific region for the SENTRY Antimicrobial Surveillance Program, 1997-1999." Clinical Infectious Diseases 32.Supplement_2 (2001): S114-S132.
Ekwall, Björn. "Screening of toxic compounds in mammalian cell cultures." Annals of the New York Academy of Sciences 407.1 (1983): 64-77.
Hoban, D. J., et al. "Worldwide prevalence of antimicrobial resistance in *Streptococcus pneumoniae*, Haemophilus influenzae, and Moraxella catarrhalis in the SENTRY Antimicrobial Surveillance Program, 1997-1999." Clinical Infectious Diseases 32.Supplement_2 (2001): S81-S93.
Kabara, Jon J., et al. "Fatty acids and derivatives as antimicrobial agents." Antimicrobial agents and chemotherapy 2.1 (1972): 23-28.
Klose, Karl E. "The suckling mouse model of cholera." Trends in microbiology 8.4 (2000): 189-191.
Sun, Cynthia Q., Charmian J. O'Connor, and Anthony M. Roberton. "The antimicrobial properties of milkfat after partial hydrolysis by calf pregastric lipase." Chemico-biological interactions 140.2 (2002): 185-198.
Written Opinion; dated Apr. 19, 2016 for PCT Application No. PCT/CA2016/050055.
International Search Report; dated Apr. 16, 2016 for PCT Application No. PCT/CA2016/050055.
Written Opinion; dated Feb. 8, 2017 for PCT Application No. PCT/CA2016/050055.
International Preliminary Report on Patentability; dated May 18, 2017 for PCT Application No. PCT/CA2016/050055.
Extended European Search Report; dated Oct. 19, 2018 for EP Application No. 16739714.0.
JP Notification of Reasons for Refusal; dated Mar. 5, 2019 for JP Application No. 2017-557236.
Compound Summary for CID 5282714, 2-Octenoic acid, (2E)-; Mar. 27, 2005.
Compound Summary for CID 61743, 9-Decenoic acid, Sep. 16, 2004.
Examination Report for corresponding New Zealand application No. 734881; dated Jan. 13, 2021 (4 pages).
Examination Report for corresponding New Zealand application No. 734881; dated Aug. 11, 2021 (2 pages).

\* cited by examiner

ANTI-BACTERIAL COMPOSITIONS

FIELD OF THE INVENTION

This invention pertains to the field of anti-bacterial compositions and, in particular, to anti-bacterial compositions comprising one or more fatty acids, one or more hydroxy acids and one or more amino alcohols.

BACKGROUND OF THE INVENTION

There is currently an urgent need for compounds and/or compositions with broad-spectrum anti-bacterial activity. The increasing incidence of infectious disease caused by bacterial pathogens in both communities and hospitals is a worldwide health concern. Severe invasive infections are reported as the main complication in cancer therapies, as well as bone marrow transplantation and major surgeries. Infection is also a major concern for immuno-compromised patients with haematological malignancy and/or AIDS.

Amongst bacterial pathogens, there has recently been a significant increase of multi-drug resistance. For example, strains of *Staphylococcus aureus* (methicillin-resistant or MRSA) and coagulase-negative Staphylococci (CoNS) have become resistant to the most commonly used antibiotics, such that the only available antibiotics uniformly active against them are the glycopeptides, vancomycin and teicoplanin. *S. aureus* is one of the leading causes of hospital-acquired bacteremia capable of causing a wide range of diseases ranging from superficial skin infections to potentially fatal illnesses such as bloodstream infection, endocarditis and pneumonia (Diekema et al. *Clin. Infect. Dis.* 2001, 32:S114-132). Other human pathogens that have begun to develop resistance to multiple antibiotics include *Streptococcus pneumoniae* (the leading cause of nosocomial infections) and *Pseudomonas aeruginosa, Haemophilus influenzae* and *Moraxella catarrhalis* (the most common community-acquired respiratory pathogens; Hoban et al. *Clin. Infect. Dis.* 2001, 32:S81-93).

These multidrug resistant bacteria ("superbugs") are not restricted to hospitals alone and they can be found in diverse settings including daycares, schools, prisons, sports facilities, airports, healthcare facilities, retirement homes, etc. Paper and plastics are indispensable to society and therefore need to be treated with antimicrobials to assist in the elimination of these "superbugs".

Thus, new anti-bacterial compositions are needed to address both the growing resistance amongst microbes to present therapies and the general lack of efficacy of existing antibiotics against microorganisms.

In the cosmetics and food industry also there is a constant need for agents having antimicrobial properties, in particular for the preservation of products which are otherwise perishable, but also for direct cosmetic or therapeutic treatment of microorganisms which can have an adverse influence on the human or animal body. Reference may be made by way of example to microorganisms which can cause body odour, acne, mycoses or the like.

The antimicrobial properties of free fatty acids have been known for many years (Kabara J. et al. *Antimicrobial Agents and Chemotherapy*, July 1972; 2(1): pp 23-28). Bergson et al. (*Antimicrobial Agents and Chemotherapy*, November 2001, pp 3209-3212), reported that both capric and lauric acid were effective in killing the yeast *Candida albicans*. Sun et al. (*Chemico-Biological Interactions* 140 (2002), pp 185-198), identified the superior microbicidal properties of caprylic, capric and lauric acid, concluding that lauric was most potent against gram positive bacteria while caprylic was optimal against gram negative organisms.

WO 2011/061237 discloses antimicrobial compositions comprising free fatty acids emulsified with membrane lipids or hydrolysed derivatives thereof, and pharmaceutical formulations comprising same. The compositions can be used in the treatment or prophylaxis of microbial infections. They can also regulate the rate of blood clotting rendering them suitable for incorporation in catheter locking solutions and for use in wound care.

WO 99/51218 discloses a biocidal composition of a blend of acids substantially free of benzoic acid or a derivative thereof and comprising a mixture of lactic acid and at least one other acid selected from formic acid, acetic acid and propionic acid. In GB 1,194,863 preservative composition for crops is described comprising 70 wt. % phosphoric acid, 20 wt. % propionic acid and 5 wt. % lactic acid.

U.S. Pat. No. 7,727,568 discloses an antimicrobial composition comprising a mixture of at least 20 wt. % lactic acid or a derivative thereof and an inorganic acid selected from a nitrogen, sulfur, and phosphorous acid, and mixtures thereof for use in animal nutrition. The composition can further comprise at least one other acid selected from acetic acid, fumaric acid, gluconic acid, (iso)butyric acid, sorbic acid, (iso)valeric acid, maleic acid, malic acid, capronic acid, benzoic acid, and citric acid.

WO2014/035246 discloses antimicrobial compositions comprising at least one free fatty acid or a derivative and/or a pharmaceutically acceptable salt thereof, at least one carboxylic acid or a pharmaceutically acceptable salt thereof; and/or at least one carbohydrate or a pharmaceutically acceptable salt thereof, wherein the carbohydrate is selected from a hydrogenated carbohydrate, a monosaccharide, a disaccharide, a polysaccharide and combinations thereof. The compositions of this reference are aimed to provide an antimicrobial composition for treating or preventing the first stage in pathogenesis in order to prevent infections. This reference also discloses that a composition comprising a combination of at least one free fatty acid and at least one carboxylic acid exhibit disinfecting properties, whereas the combination of at least one free fatty acid and at least one carbohydrate, optionally in combination with at least one carboxylic acid, exerts a dual antimicrobial effect.

WO2009/140062 discloses use of amino alcohols as additives for hydrocarbonaceous compositions, such as petroleum and fuels, to improve the corrosion and microbial resistance of hydrocarbonaceous compositions. This reference also discloses that the particularly preferred amino alcohols for the desired result are 2-amino-2-methyl-1-hexanol, 2-amino-2-ethyl-1-pentanol, 2-amino-2-methyl-1-octanol, 2-amino-2-ethyl-1-heptanol, 2-amino-2-propyl-1-hexanol, (1-aminocyclohexyl)methanol, (1-aminocyclooctyl)methanol, 2-amino-2-phenyl-1-propanol, (1-aminocyclopentyl)methanol, and mixtures thereof.

There remains a need for antimicrobial compounds and/or compositions that have improved and/or broad spectrum anti-bacterial activity.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

It is an object of the present invention to provide a novel composition having improved anti-bacterial activity. In accordance with an aspect of the present invention, there is provided an antibacterial composition comprising at least one unsaturated fatty acid or a pharmaceutically acceptable salt thereof, wherein the free fatty acid is selected from a free fatty acid having from 6 to 16 carbon atoms; at least one alpha-hydroxy acid or a pharmaceutically acceptable salt thereof; and at least one amino alcohol.

In accordance with another aspect of the present invention, there is provided a pharmaceutical formulation comprising a composition as defined above, and a pharmaceutically acceptable carrier.

In accordance with another aspect of the present invention, there is provided a use of the pharmaceutical formulation of the present invention for inhibiting growth and/or proliferation of a microbe.

In accordance with another aspect of the present invention, there is provided a method of killing and/or inhibiting the growth of microbes on a substrate comprising applying an effective amount of the antibacterial composition as defined above.

DETAILED DESCRIPTION OF THE INVENTION

The present invention provides novel anti-bacterial compositions and uses thereof. In the context of the present invention, the term "anti-bacterial" refers to the inhibition, prevention or eradication of the growth or proliferation of bacteria and to the inhibition, prevention or eradication of the growth or proliferation of bacterial cells.

Definitions

Unless defined otherwise, all technical and scientific terms used herein have the same meaning as commonly understood by one of ordinary skill in the art to which this invention pertains.

The term "alkyl" refers to a straight chain or branched, alkyl group of one to ten carbon atoms. This term is further exemplified by such groups as methyl, ethyl, n-propyl, i-propyl, n-butyl, t-butyl, 1-butyl (or 2-methylpropyl), and the like.

The term "amino" refers to the group NRR', where R and R' may independently be hydrogen, lower alkyl, or substituted alkyl.

The terms "therapy" and "treatment," as used interchangeably herein, refer to an intervention performed with the intention of alleviating the symptoms associated with, preventing the development of, or altering the pathology of a disease, disorder or condition.

Thus, the terms therapy and treatment are used in the broadest sense, and include the prevention (prophylaxis), moderation, management, reduction, or curing of a disease, disorder or condition at various stages. Prevention or reduction of the progression of a disease, disorder or condition is encompassed by these terms. Also encompassed by these terms is an intervention resulting in an alteration of physiology and/or biochemistry of a living subject. Those in need of therapy/treatment include those already having the disease, disorder or condition as well as those prone to, or at risk of developing, the disease, disorder or condition and those in whom the disease, disorder or condition is to be prevented. The therapeutic application of compounds of the invention, therefore, refers to a therapy or treatment, as defined herein.

The terms "subject" or "patient," as used herein, refer to an animal in need of treatment, including humans and other mammals.

Administration of the composition of the present invention "in combination with" one or more further therapeutic agents, is intended to include simultaneous (concurrent) administration and consecutive administration. Consecutive administration is intended to encompass various orders of administration of the therapeutic agent(s) and the compound(s) to the subject.

The term "inhibit," as used herein, means to reduce, halt or hold in check, and thus inhibition may be complete or partial and may be of short or long term duration. The term may be used in the context of inhibiting a process or action already begun or it may be used in the context of inhibiting initiation of a process or action.

As used herein, the term "about" refers to approximately a +/−10% variation from a given value. It is to be understood that such a variation is always included in any given value provided herein, whether or not it is specifically referred to.

The Compositions

The present invention provides an antibacterial composition comprising at least one unsaturated fatty acid or a pharmaceutically acceptable salt thereof; at least one alpha-hydroxy carboxylic acid or a pharmaceutically acceptable salt thereof; and at least one amino alcohol.

The unsaturated fatty acids of the present invention have from 6 to 16 carbon atoms, preferably the free fatty acid has from 8 to 12 carbon atoms. In one embodiment, the free fatty acid is undecylenic acid.

The alpha hydroxy acids of the present invention can be selected from glycolic acid, lactic acid, citric acid, mandelic acid, oxalic acid, and malonic acid. In one embodiment, the alpha hydroxy acid is lactic acid.

The amino alcohol of the present invention can have a formula:

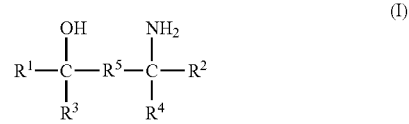

wherein $R^1$ and $R^3$ are each independently H, linear or branched alkyl, $R^2$ and $R^4$ are each independently H, linear or branched alkyl; and $R^5$ is absent or is a $C_1$-$C_6$ alkylene.

In one embodiment, in the formula (I) above, $R^5$ is absent, $R^2$ and $R^4$ are both C1-C6 alkyl. In one embodiment, the amino alcohol is 2-amino-2-methyl-1-propanol.

In one embodiment, in the formula (I) above, $R^5$ is absent, $R^2$ is C1-C6 alkyl and $R^4$ is $CH_2OH$.

In one embodiment, the amino alcohol is amino methyl propane diol (AMPD).

In one embodiment, the amino alcohol is monoethanolamine (MEA).

The individual concentrations of unsaturated fatty acid, alpha hydroxy acid and amino alcohol can be in the range of about 5% to about 90% by weight of the total weight of the composition.

In one embodiment the concentration of the unsaturated fatty acid is about 5%, 10%, 15%, 20%, 25%, 30%, 235%, 40%, 45%, 50%, 55%, 60%, 65%, 70%, 75%, 80%, 85%, 90% or a percentage between any two of these values.

In one embodiment the concentration of the alpha hydroxy acid is about 5%, 10%, 15%, 20%, 25%, 30%, 235%, 40%, 45%, 50%, 55%, 60%, 65%, 70%, 75%, 80%, 85%, 90% or a percentage between any two of these values.

In one embodiment the concentration of the amino alcohol is about 5%, 10%, 15%, 20%, 25%, 30%, 235%, 40%, 45%, 50%, 55%, 60%, 65%, 70%, 75%, 80%, 85%, 90% or a percentage between any two of these values.

In one embodiment, in the composition of the present invention the amount of alpha hydroxy acid is in the range of about 10% to about 40% by weight of the total weight of the composition, the amount of unsaturated fatty acid is in the range of about 40% to about 80% by weight of the total weight of the composition, and the amount of amino alcohol is in the range of about 5% to about 25% by weight of the total weight of the composition. In one embodiment, in the composition of the present invention the amount of alpha hydroxy acid is in the range of about 20% to about 30% by weight of the total weight of the composition, the amount of unsaturated fatty acid is in the range of about 50% to about 70% by weight of the total weight of the composition, and the amount of amino alcohol is in the range of about 10% to about 15% by weight of the total weight of the composition. In one embodiment, in the composition of the present invention the amount of alpha hydroxy acid is in the range of about 10% to about 15% by weight of the total weight of the composition, the amount of unsaturated fatty acid is in the range of about 50% to about 70% by weight of the total weight of the composition, and the amount of amino alcohol is in the range of about 20% to about 30% by weight of the total weight of the composition In one embodiment, the composition of the present invention comprises about 28.00 wt. % of alpha hydroxy acid, about unsaturated fatty acid 58.00 wt. % and about 14.00 wt. % of amino alcohol (95%). In one embodiment, the composition of the present invention comprises about 25.00 wt. % of alpha hydroxy acid, about unsaturated fatty acid 55.00 wt. % and about 20.00 wt. % of amino alcohol (95%). In one embodiment, the composition of the present invention comprises about 30.00 wt. % of alpha hydroxy acid, about unsaturated fatty acid 60.00 wt. % and about 10.00 wt. % of amino alcohol (95%).

The antibacterial composition may further comprise at least one viscosity-enhancing agent, i.e. thickening agent. Preferably the viscosity-enhancing agent is selected from xanthan gum, alginic acid, agar, carrageenan, locust bean gum, pectin, cellulose derivatives, gelatin and combinations thereof.

The antibacterial composition may comprise at least one emulsifying agent, such as polysorbate (Tween) 20, polysorbate 40, polysorbate 60, polysorbate 80, polyoxyethylene glycol alkyl ethers, glucoside alkyl ethers, polyoxyethylene glycol octylphenol ethers, polyoxyethylene glycol alkylphenol ethers, glycerol alkyl esters, poloxamers, polyoxyl castor oil, and combinations thereof. More preferably the emulsifying agent is polysorbate 80.

Uses of the Anti-Bacterial Compositions

The present invention provides for the use of the compositions disclosed herein for the inhibition, prevention or eradication of the growth and/or proliferation of bacteria, either alone or in combination with known anti-microbial agents.

In one embodiment, the present invention provides a method of inhibiting bacterial growth by contacting a bacterium with an effective amount of a composition as disclosed herein.

The compositions have broad spectrum anti-bacterial activity, in which case they may be used against gram-positive and/or gram-negative bacteria.

Examples of gram-positive bacteria include, *Clostridium difficile*, *Clostridium perfringens*-vegetative cells, *Clostridium sporogenes*-vegetative cells, *Enterococcus faecalis*-vancomicyn resistant (VRE), *Enterococcus faecium*, *Micrococcus luteus*, *Mycobacterium smegmatis*, *Staphylococcus aureus*, *Staphylococcus aureus*-methicillin resistant (MRSA), *Staphylococcus aureus*-vancomicyn resistant (VRSA), *Staphylococcus epidermidis*, *Staphylococcus haemolyticus*, *Staphylococcus hominis*, *Staphylococcus saprophyticus*, *Streptococcus agalactiae*, *Streptococcus pneumonia*, *Streptococcus pneumoniae*-Drug Resistant, *Streptococcus pyogenes*, *Streptococcus*-Group A-Erythromycin-resistant, *Streptococcus*-Group B-Clindamycin-resistant and *Pseudomonas aeruginosa*, *Streptococcus pyogenes* and/or *Streptococcus faecalis*.

Examples of gram-negative bacteria include *Acinetobacter baumannii*, *Acinetobacter*—multi drug resistant, *Bacteroides fragilis*, *Bordetella pertussis*, *Burkholderia cepacia*, *Camplylobacter* species, *Camplylobacter*—drug resistant, *Enterobacter aerogenes*, Enterobacteriaceae (ESBLs), Enterobacteriaceae—carbapenem-resistant, *Escherichia coli* (cfu/g) $4.4 \times 10^5$, *Escherichia coli* (*E. coli*)—(Resistant), *Haemophilus influenza*, *Helicobacter pylori*, *Klebsiella oxytoca*, *Klebsiella pneumoniae* pneumoniae (CRE), *Neisseria gonorrhoeae*, *Neisseria gonorrhoeae*—drug resistant, *Neisseria meningitides*, *Proteus mirabilis*, *Pseudomonas aeruginosa* (cfu/g) $3.5 \times 10^5$, *Pseudomonas aeruginosa* (Regular), *Pseudomonas aeruginosa*—multi drug resistant, *Salmonella*-non-typhoidal-drug resistant, *Salmonella typhi*, *Salmonella typhi*-drug resistant, *Serratia marcescens*, *Shigella sonnei*, *Shigella*—drug-resistant, *Vibrio cholerae*, *Enterobacter*, and/or *Klebsiella pneumonia*.

In one embodiment, examples of bacteria that may be inhibited by the compositions of the present invention include, but are not limited to, *Enterobacter faecalis*, *Enterococcus faecium*, *Escherichia coli*, *Escherichia coli* O157:H7, *Escherichia coli* (cfu/g) $4.4 \times 10^5$, *Staphylococcus aureus*, *Staphylococcus aureus* K147, *Staphylococcus epidermidis*, *Pseudomonas aeruginosa* and *Klebsiella pneumonia*.

It is well-established in the field of microbiology that many multidrug-resistant strains of bacteria have emerged in the recent past and will continue to emerge with the continued use of standard antibiotics. Examples of currently known resistant strains of bacteria include methicillin-resistant *Staphylococcus aureus* (MRSA), and vancomycin-resistant *Enterococcus faecium*.

In one embodiment, the compositions of the present invention can be used to inhibit growth of such multidrug-resistant strains. In one embodiment, the compositions of the present invention are used to inhibit the growth of MRSA and/or *Enterococcus faecium*.

In one embodiment, the compositions of the present invention are used in the preparation of antibiotic compositions.

The compositions of the present invention can be used as the active ingredient in anti-bacterial cleansers, polishes, paints, sprays, soaps, or detergents. In such cases, antibacterial composition of the present invention can generally be used in quantities of between about 0.1% and about 20% by weight of the final product. In one embodiment, the amount of antibacterial composition is about 0.1% to 5% by weight. In one embodiment the amount of antibacterial composition is about 0.3% to about 5% by weight.

These compositions can also be included as an antibacterial agent in cosmetic, personal care, household and industrial products, for example, to improve shelf-life by inhibiting the growth of microbes within the products.

The compositions may be formulated for application to surfaces to inhibit the growth of a bacterial species thereon, for example, surfaces such as countertops, desks, chairs, laboratory benches, tables, floors, sinks, showers, toilets, bathtubs, bed stands, tools or equipment, doorknobs and windows. Alternatively, the compositions may be formulated for laundry applications, for example, for washing clothes, towels, sheets and other bed linen, washcloths or other cleaning articles.

The antibacterial cleansers, polishes, paints, sprays, soaps, or detergents according to the present invention can optionally contain suitable solvent(s), carrier(s), thickeners, pigments, fragrances, deodorisers, emulsifiers, surfactants, wetting agents, waxes, or oils. The cleansers, polishes, paints, sprays, soaps, and detergents according to the present invention are useful in institutions, such as in hospital settings for the prevention of nosocomial infections, as well as in home settings.

In addition, the invention contemplates the use of the compositions in formulations to kill or inhibit the growth of bacterial species in food preparations, or to sterilise surgical and other medical equipment and implantable devices, including prosthetic joints. The compositions can also be formulated for use in the in situ sterilisation of indwelling invasive devices such as intravenous lines and catheters, which are often foci of infection.

The present invention further contemplates the use of these compositions as the active ingredient in personal care items, such as soaps, deodorants, shampoos, mouthwashes, toothpastes, and the like. Many compositions used in personal care applications are susceptible to bacterial growth and it is thus desirable to incorporate into these compositions an effective anti-bacterial material.

In one embodiment, the present invention provides a formulation containing a composition as defined herein for external use as a pharmaceutically acceptable skin cleanser. In one embodiment, the compositions of the present invention can also be used as dermocosmetic compositions.

The anti-bacterial agent may be incorporated into the personal care formulation using techniques known in the art. Thus, the anti-bacterial agent may be added to the personal care formulation as a solution, emulsion or dispersion in a suitable liquid medium. Alternatively, the anti-bacterial agent may be added, undiluted, to the personal care formulation or may be added with a solid carrier or diluent. The anti-bacterial agent may be added to the pre-formed personal care formulation or may be added during the formation of the personal care formulation, either separately or premixed with one of the other components of the formulation.

The antibacterial composition of the present invention can generally be used in quantities of between 0.1% and 20% by weight of the personal care compositions. In one embodiment, the amount of antibacterial composition is between 0.1% and 5% by weight. In one embodiment the amount of antibacterial composition is about 0.3% to about 5% by weight.

Pharmaceutical Formulations and Administration of Anti-Bacterial Compositions

For use as therapeutic agents in the treatment of bacterial infections, or disorders or diseases associated therewith in a subject, the anti-bacterial compositions of the present invention are typically formulated prior to administration. Therefore, the present invention provides pharmaceutical formulations comprising one or more compositions of the present invention and a pharmaceutically-acceptable carrier, diluent, or excipient. The present pharmaceutical formulations are prepared by standard procedures using well-known and readily available ingredients. In making the compositions of the present invention, the active ingredient will usually be mixed with a carrier, or diluted by a carrier, or enclosed within a carrier, and may be in the form of a capsule, sachet, paper, or other container.

The pharmaceutical formulations comprising the anti-bacterial compositions according to the present invention may be formulated in a number of ways depending upon the desired treatment and upon the area to be treated. Administration may be topical (including ophthalmic and to mucous membranes including vaginal and rectal delivery), pulmonary, e.g. by inhalation or insufflation of powders or aerosols, including by nebulizer; intratracheal, intranasal, epidermal and transdermal, oral or parenteral. Parenteral administration includes intravenous, intraarterial, subcutaneous, intraperitoneal or intramuscular injection or infusion; or intracranial, e.g. intrathecal or intraventricular, administration.

For administration to an individual for the treatment of an infection or disease, the present invention also contemplates the formulation of the pharmaceutical formulations comprising the anti-bacterial composition into oral dosage forms such as tablets, capsules and the like. For this purpose, the composition can be combined with conventional carriers, such as magnesium carbonate, magnesium stearate, talc, sugar, lactose, pectin, dextrin, starch, gelatine, tragacanth, methylcellulose, sodium carboxymethyl-cellulose, low melting wax, cocoa butter and the like. Diluents, flavouring agents, solubilizers, lubricants, suspending agents, binders, tablet-disintegrating agents and the like can also be employed, if required. The anti-microbial compositions can be encapsulated with or without other carriers. In accordance with the present invention, the proportion of anti-bacterial composition(s) in any solid and liquid formulation will be at least sufficient to impart the desired activity to the individual being treated upon oral administration. The present invention further contemplates parenteral injection of the anti-bacterial compositions, in which case the compositions are formulated as a sterile solution containing other solutes, for example, enough saline or glucose to make the solution isotonic.

For administration by inhalation or insufflation, the anti-microbial compositions can be formulated into an aqueous or partially aqueous solution, which can then be utilized in the form of an aerosol. Aqueous formulations of the anti-bacterial compositions of the present invention may also be used in the form of ear or eye drops, or ophthalmic solutions. The present invention further contemplates topical use of the anti-bacterial compositions. For this purpose they can be formulated as dusting powders, creams or lotions in pharmaceutically acceptable vehicles, which are applied to affected portions of the skin.

Compositions intended for oral use may be prepared according to procedures known in the art for the manufacture of pharmaceutical formulations and such formulations may further contain one or more sweetening agents, flavouring agents, colouring agents, preserving agents, or a combination thereof, in order to provide pharmaceutically elegant and palatable preparations. Tablets typically contain the anti-bacterial composition(s) in admixture with non-toxic pharmaceutically acceptable excipients suitable for the manufacture of tablets, such as inert diluents, for example, calcium carbonate, sodium carbonate, lactose, calcium phosphate or sodium phosphate; granulating and disintegrating agents, for example, corn starch, or alginic acid; binding agents, for example, starch, gelatine or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatine capsules wherein the anti-bacterial composition(s) is mixed with an inert solid diluent, for example, calcium carbonate, calcium phosphate or kaolin, or as soft gelatine capsules wherein the active ingredient is mixed with water or an oil medium, for example, peanut oil, liquid paraffin or olive oil.

Aqueous suspensions typically contain the anti-bacterial composition(s) in admixture with excipients suitable for the manufacture of aqueous suspensions, such as suspending agents (for example, sodium carboxylmethylcellulose, methyl cellulose, hydropropylmethyl cellulose, sodium alginate, polyvinylpyrrolidone, gum tragacanth and gum acacia); dispersing or wetting agents such as a naturally-occurring phosphatide (for example, lecithin), or condensation products of an alkylene oxide with fatty acids (for example, polyoxyethylene stearate), or condensation products of ethylene oxide with long chain aliphatic alcohols (for example, hepta-decaethyleneoxycetanol), or condensation products of ethylene oxide with partial esters derived from fatty acids and a hexitol (for example, polyoxyethylene sorbitol monooleate), or condensation products of ethylene oxide with partial esters derived from fatty acids and hexitol anhydrides (for example, polyethylene sorbitan monooleate). The aqueous suspensions may further contain one or more preservatives, for example, ethyl, or n-propyl-p-hydroxy benzoate; one or more colouring agents; one or more flavouring agents, or one or more sweetening agents, such as sucrose or saccharin, or a combination thereof.

Oily suspensions may be formulated by suspending the anti-bacterial composition(s) in a vegetable oil, for example, peanut oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide palatable oral preparations. These compositions may be preserved by the addition of an anti-oxidant such as ascorbic acid.

Dispersible powders and granules suitable for preparation of an aqueous suspension by the addition of water provide the anti-bacterial composition in admixture with a dispersing or wetting agent, suspending agent and one or more preservatives. Suitable dispersing or wetting agents and suspending agents are exemplified by those mentioned above. Additional excipients, for example, sweetening, flavouring and colouring agents, may also be present.

Pharmaceutical formulations of the present invention may also be in the form of oil-in-water emulsions. The oil phase may be a vegetable oil, for example, olive oil or peanut oil, or a mineral oil, for example, liquid paraffin, or mixtures thereof. Suitable emulsifying agents may be naturally-occurring gums (for example, gum acacia or gum tragacanth); naturally-occurring phosphatides (for example, soy bean lecithin), and esters or partial esters derived from fatty acids and hexitol anhydrides (for example, sorbitan monooleate), and condensation products of the partial esters with ethylene oxide (for example, polyoxyethylene sorbitan monooleate). The emulsions may also contain sweetening and flavouring agents.

Syrups and elixirs may be formulated with sweetening agents, for example, glycerol, propylene glycol, sorbitol or sucrose. Such formulations may also contain one or more demulcents, preservatives or flavouring and colouring agents, or combinations thereof.

The pharmaceutical formulations may be in the form of a sterile injectable aqueous or oleaginous suspension. This suspension may be formulated according to known art using suitable dispersing or wetting agents and suspending agents as described above. The sterile injectable preparation may also be a solution or a suspension in a non-toxic, parentally acceptable diluent or solvent, for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. Typically, a bland fixed oil is employed for this purpose such as a synthetic mono- or diglyceride. In addition, fatty acids such as oleic acid find use in the preparation of injectables. Adjuvants, such as local anaesthetics, preservatives and buffering agents, may also be included in the injectable formulation.

The composition(s) of the present invention may be administered, together or separately, in the form of suppositories for rectal or vaginal administration of the composition. These compositions can be prepared by mixing the composition with a suitable non-irritating excipient which is solid at ordinary temperatures but liquid at the rectal/vaginal temperature and will therefore melt to release the composition. Examples of such materials include cocoa butter and polyethylene glycols.

Another formulation of the present invention employs transdermal delivery devices ("patches"). Such transdermal patches may be used to provide continuous or discontinuous administration/application of the anti-bacterial compositions of the present invention in controlled amounts. The construction and use of transdermal patches for the delivery of pharmaceutical agents is well known in the art (see, for example, U.S. Pat. No. 5,023,252; issued Jun. 11, 1991, incorporated herein by reference in its entirety). Such patches may be constructed for continuous, pulsatile, or on demand delivery of pharmaceutical agents.

In one embodiment, the composition(s) of the present invention can be incorporated into medical dressings such as Tegaderm pad from 3M (which act as traditional sponge gauze, a bacterial barrier just helping to reduce the risk of infection). In Tegaderm structure, the main biocompatible wound dressing part is made of cellulose paper fibre coated with silicone material, and all supporting and adhering parts are made of synthetic materials such as: polyethylene, polyurethane, polyester and acrylate polymer.

It may be desirable or necessary to introduce the pharmaceutical formulations to the brain, either directly or indirectly. Direct techniques usually involve placement of a drug delivery catheter into the host's ventricular system to bypass the blood-brain barrier. An example of such an implantable delivery system, used for the transport of biological factors to specific anatomical regions of the body, is described in U.S. Pat. No. 5,011,472, incorporated herein by reference in its entirety.

The dosage of the anti-bacterial composition to be administered is not subject to defined limits, but will usually be an effective amount. In general, the dosage will be the equivalent, on a molar basis, of the pharmacologically active free form produced from a dosage formulation upon the metabolic release of the active free drug to achieve its desired pharmacological and physiological effects. The pharmaceutical compositions are typically formulated in a unit dosage form, each dosage containing from, for example, about 0.05 to about 100 mg of the anti-bacterial composition. The term "unit dosage form" refers to physically discrete units suitable as unitary dosages for administration to human subjects and other animals, each unit containing a predetermined quantity of anti-bacterial composition calculated to produce the desired therapeutic effect, in association with a suitable pharmaceutical excipient.

Typical daily dosages of the anti-bacterial compositions fall within the range of about 0.01 to about 200 mg/kg of body weight in single or divided dose. However, it will be understood that the amount of the composition actually administered will be determined by a physician, in the light of the relevant circumstances, including the condition to be treated, the chosen route of administration, the actual composition administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, for example, by first dividing larger doses into several smaller doses for administration throughout the day.

Compositions of the present invention formulated for topical administration are suitable in the treatment and/or prevention of bacterial infections of the skin and mucosa.

Topical pharmaceutical and/or dermocosmetic formulations according to the invention comprise the antibacterial composition mixed with one or more suitable excipients and may be, for example, in the form of cream, ointment, gel, gum, toothpaste, mouthwash or shampoo.

The pharmaceutical formulations and/or the dermocosmetic formulations can comprise about 0.1% to about 20% by weight of the antibacterial composition of the present invention. In one embodiment, the amount of antibacterial composition is about 0.1% to about 10% by weight. In one embodiment, the amount of antibacterial composition is about 0.1% to about 5% by weight. In one embodiment the amount of antibacterial composition is about 0.3% to about 2% by weight.

Examples of suitable excipients that may be used in the compositions according to the invention are solvents, diluents, gliding agents, preservatives, gums, sweeteners, coating agents, binders, disintegrating agents, lubricants, suspending agents, dispersing agents, colorants, flavouring agents, non-stick agents, surfactants, plasticisers, emulsifiers, chelating agents and emollients.

The solvent preferably used is water, but alcohols or other organic solvents may also be used, possibly mixed with water.

The choice of excipients is part of the normal knowledge of one skilled in the art, and will mainly depend on the pharmaceutical and/or dermocosmetic form chosen.

For example, a cream can be prepared by incorporating the anti-bacterial composition of the present invention in a topical carrier consisting of liquid paraffin, dispersed in an aqueous medium by means of lubricants. An ointment can be prepared by mixing TSP with a topical carrier such as mineral oil or wax. A gel can be prepared by mixing TSP with a topical carrier containing a gelling agent.

The pharmaceutical and/or dermocosmetic composition according to the invention may also be a, woven or nonwoven, material coated and/or impregnated with a mixture of the anti-bacterial composition with a suitable carrier or a matrix in which the anti-bacterial composition is dispersed so that it comes into contact with the skin for transdermal administration. Specific examples are bandage, gauze, towelettes, etc.

The choice of type of pharmaceutical and/or dermocosmetic form will depend mainly on the area to be treated and is part of the normal knowledge of one skilled in the art. For example, a gum or mouthwash may be more suitable to treat the oral cavity, whereas a cream, ointment, lotion or towelettes may be suitable for the skin of the face.

The term "skin" is used according to the present in its conventional meaning, namely an external organ including the epithelial tissue. The term "mucosa" is also used with its usual meaning, which relates to all the mucosal barriers in the body, such as the gastrointestinal, pulmonary, sublingual, buccal, rectal, vaginal, nasal, urethral and ocular barriers.

The compositions according to the invention are preferably applied by topical administration directly to the area of the skin or mucosa which presents, or is assumed to present, a bacterial infection or other disorders caused by the presence of microbes. The infection often originates in a part of the skin or mucosa which presents a lesion, such as a wound, laceration or burn. In such case, the composition according to the invention can be applied directly to the lesion and/or the surrounding area.

The compositions of the present invention can also be used in the treatment and/or prevention of several disorders of the skin and mucosa, which are known to be caused by bacteria, for example, psoriasis, eczema, acne, etc. Other treatments may include wound care, and burn care, etc.

Anti-Bacterial Activity of Compositions

The anti-bacterial activity of a candidate composition can be tested using standard techniques known in the art. As is known in the art, anti-bacterial activity of a composition or composition may result in the killing of bacterial cells (i.e. bacteriocidal activity), or it may result in the slowing or arrest of the growth of bacterial cells (i.e. bacteriostatic activity). Thus the compositions of the present may be bacteriocidal and/or bacteriostatic.

Compositions of the present invention that slow or arrest bacterial cell growth may be useful in combination treatments with other known anti-bacterial agents.

In vitro Testing

In vitro methods of determining the ability of candidate compositions to inhibit, prevent or eradicate the growth of bacterial cells are well-known in the art. In general, these methods involve contacting a culture of the cells of interest with various concentrations of the candidate composition and monitoring the growth of the cell culture relative to an untreated control culture. A second control culture comprising cells contacted with a known anti-bacterial agent may also be included in such tests, if desired.

Anti-bacterial effects can be expressed as the percentage (%) inhibition of growth of a given micro-organism over a pre-determined period of time by treatment with a single concentration of a candidate composition. This method provides a rapid method of assessing the ability of a composition to inhibit bacterial growth, for example, prior to conducting more in-depth tests, such as MIC determinations or in vivo testing. An example of such an testing is in-vitro Time-Kill Method which is well known in the art.

Toxicity Testing

It is important that the anti-bacterial compositions of the present invention exhibit low toxicity.

In vitro acute toxicity testing of a composition of the present invention can be performed using mammalian cell lines (see, for example, Ekwall, B., Ann. N.Y. Acad. Sci., (1983) 407:64-77). Selection of an appropriate cell line is dependent on the potential application of the candidate composition and can be readily determined by one skilled in the art.

In vivo toxicity testing can be performed by standard methodology, for example, by injecting or introducing varying concentrations of the candidate composition into an appropriate animal model. The composition can be injected once, or administration can be repeated over several days. The toxic effects of the composition can be evaluated over an appropriate time period by monitoring the general health and body weight of the animals. After the completion of the period of assessment, the animals can be sacrificed and the appearance and weight of the relevant organs determined.

In vivo Testing

The ability of a test composition to act as an anti-bacterial agent can also be tested in vivo using standard techniques. A number of animal models are known in the art that are suitable for testing the activity of anti-bacterial compositions and are readily available.

Methods for conducting in vivo tests to determine the activity of anti-bacterial compositions are well-known in the art. Typically, in vivo testing comprises introducing a selected micro-organism into the appropriate animal model in a sufficient amount to cause infection, followed by administration of one or more doses of the test composition. Methods of administration will vary depending on the composition being employed, but can be, for example, by way of bolus infusion into a suitable vein (such as the tail vein of mice or rats), or by oral administration. Animals treated with a known anti-bacterial agent and/or with a saline or buffer control solution serve as controls. Repeat doses of the test composition may be administered to the animal, if necessary, at appropriate time intervals. The animals are subsequently monitored daily for mortality.

Additional Tests

In addition to the above tests, the compositions of the invention can be submitted to other standard tests, such as stability tests, bioavailability tests and the like. As will be readily apparent to one skilled in the art, compositions in accordance with the present invention will need to meet certain criteria in order to be suitable for human use and to meet regulatory requirements. Thus, once a composition of the invention has been found to be suitable for animal administration, standard in vitro and in vivo tests can be conducted to determine information about the metabolism and pharmacokinetic (PK) of the compositions and combinations (including data on drug-drug interactions where appropriate) which can be used to design human clinical trials.

To gain a better understanding of the invention described herein, the following examples are set forth. It should be understood that these examples are for illustrative purposes only.

Therefore they should not limit the scope of the invention in any way.

EXAMPLES

An exemplary composition of the present invention (composition A) was prepared by mixing 50 grams of lactic acid, 105 grams of undecylenic acid and 25 grams of AMP-95%.

Composition A is soluble in most solvents (i.e., acetone, chloroform, methanol, ethanol, benzene, DMAC, DMSO) with no loss of bioactivity and can be solubilized in aqueous medium using a co-solvent system. Physical properties of the composition remained the same after heating (no color change or gelation or evaporation was observed).

Example 1: In Vitro Inhibition of Gram Positive Bacteria

The anti-bacterial effect of the exemplary composition A was evaluated at two different concentrations versus suspensions of *Enterococcus faecalis* VRE (ATCC #51575) and *Staphylococcus aureus aureus* MRSA (ATCC #33591).

Testing was conducted in accordance with a Non-GLP evaluation of one test material for its antibacterial properties when challenged with two microorganism species using an in-vitro Time-Kill Method. The test material was prepared at two different concentrations prior to evaluation. Test Solution #1 was prepared by diluting the test material in the ratio of 1.0 mL of concentrated test material to 100 mL of sterile Water-for-Irrigation, USP (WFI) (1:100 [v/v] dilution). Test Solution #2 was prepared by diluting the test material in the ratio of 0.1 mL of Composition A to 100 mL of WFI (1:1,000 [v/v] dilution). A 0.1 mL aliquot of a challenge suspension was inoculated into a test tube containing 9.9 mL of a Test Solution and mixed thoroughly using a vortex mixer. Each challenge suspension was exposed to each Test Solution for 10 minutes, timed using a calibrated minute/second timer. After the exposure time had elapsed, a 1.0 mL aliquot was transferred from the tube containing Test Solution/inoculum into a separate sterile test tube containing 9.0 mL of Butterfield's Phosphate Buffer solution with product neutralizers (BBP++), and mixed thoroughly using a vortex mixer. Ten-fold dilutions were prepared in neutralizing solution, mixing thoroughly using a vortex mixer between dilutions. 1.0 mL and/or 0.1 mL aliquots of each dilution were pour-plated, in duplicate, using Tryptic Soy Agar with product neutralizers (TSA+).

Tables 1 and 2 present the initial population (CFU/mL) and post-exposure populations (CFU/mL) of each challenge species, and the $Log_{10}$ and percent reductions produced by each Test Solution following a 10-minute exposure.

TABLE 1

Test Solution #1 - Composition A
1:100 [v/v] dilution[1]

| Microorganism Species (ATCC #) | Inoculum Level (CFU/mL) | Exposure Time | Post-Exposure Population | $Log_{10}$ Reduction | Percent Reduction |
|---|---|---|---|---|---|
| Enterococcus faecalis VRE (ATCC #51575) | $3.60 \times 10^7$ | 10 minutes | $<1.00 \times 10^1$ | 6.5563 | 99.9999% |
| Staphylococcus aureus aureus MRSA (ATCC #33591) | $1.1150 \times 10^7$ | 10 minutes | $1.50 \times 10^1$ | 5.8712 | 99.9999% |

TABLE 2

Test Solution #2 - Composition A
1:1,000 [v/v] dilution[1]

| Microorganism Species | Inoculum Level | Exposure | Post-Exposure Population | $Log_{10}$ | Percent |
|---|---|---|---|---|---|
| Enterococcus faecalis VRE (ATCC #51575) | $3.60 \times 10^7$ | 10 minutes | $<1.00 \times 10^1$ | 6.5563 | 99.9999% |
| Staphylococcus aureus aureus MRSA (ATCC #33591) | $1.1150 \times 10^7$ | 10 minutes | $<1.00 \times 10^1$ | 6.0473 | 99.9999% |

Notes:
[1] Concentrated Test Composition was diluted with sterile Water-for-Irrigation, USP, prior to evaluation.

Example 2: In Vitro Inhibition of Gram Negative Bacteria

The anti-bacterial effect of the test material, Composition A, was evaluated at two different concentrations versus suspensions of Escherichia coli (ATCC #BAA-2469) and Klebsiella pneumoniae pneumoniae (ATCC #BAA-2146).

Testing was conducted in accordance with a Non-GLP evaluation of one test material for its antibacterial properties when challenged with two microorganism species using an in-vitro Time-Kill Method. The test material was prepared at two different concentrations prior to evaluation. Test Solution #1 was prepared by diluting the test material (Composition A) in the ratio of 1.0 mL of concentrated test material to 100 mL of sterile Water-for-Irrigation, USP (WFI) (1:100 [v/v] dilution). Test Solution #2 was prepared by diluting the test material in the ratio of 0.1 mL of concentrated test material to 100 mL of WFI (1:1,000 [v/v] dilution). A 0.1 mL aliquot of a challenge suspension was inoculated into a test tube containing 9.9 mL of a test solution and mixed thoroughly using a vortex mixer. Each challenge suspension was exposed to each Test Solution for 10 minutes, timed using a calibrated minute/second timer. After the exposure time had elapsed, a 1.0 mL aliquot was transferred from the tube containing Test Solution/inoculum into a separate sterile test tube containing 9.0 mL of Butterfield's Phosphate Buffer solution with product neutralizers (BBP++), and mixed thoroughly using a vortex mixer. Ten-fold dilutions were prepared in neutralizing solution, mixing thoroughly using a vortex mixer between dilutions. 1.0 mL and/or 0.1 mL aliquots of each dilution were pour-plated, in duplicate, using Tryptic Soy Agar with product neutralizers (TSA+).

Tables 3 and 4 present the initial population (CFU/mL) and post-exposure populations (CFU/mL) of each challenge species, and the $Log_{10}$ and percent reductions produced by each Test Solution following a 10-minute exposure.

TABLE 3

Test Solution #1 - Composition A
1:100 [v/v] dilution[2]

| Microorganism Species (ATCC #) | Inoculum Level | Exposure Time | Post-Exposure Population | $Log_{10}$ Reduction | Percent Reduction |
|---|---|---|---|---|---|
| Escherichia coli (ATCC #BAA-2469) | $8.450 \times 10^6$ | 10 minutes | $<1.00 \times 10^1$ | 5.9269 | 99.9999% |
| Klebsiella pneumoniae pneumoniae (ATCC #BAA-2146) | $2.350 \times 10^7$ | 10 minutes | $<1.00 \times 10^1$ | 6.3711 | 99.9999% |

TABLE 4

Test Solution #2- Composition A
1:1,000 [v/v] dilution[2]

| Microorganism Species (ATCC #) | Inoculum Level (CFU/mL) | Exposure Time | Post-Exposure Population (CFU/mL) | Logw Reduction | Percent Reduction |
|---|---|---|---|---|---|
| *Escherichia coli* (ATCC #BAA-2469) | $8.450 \times 10^6$ | 10 minutes | $<1.00 \times 10^1$ | 5.9269 | 99.9999% |
| *Klebsiella pneumoniae pneumoniae* (ATCC #BAA-2146) | $2.350 \times 10^7$ | 10 minutes | $<1.00 \times 10^1$ | 6.3711 | 99.9999% |

Notes:
[2] Concentrated Test Product (composition A) was diluted with sterile Water-for-Irrigation, USP, prior to evaluation.

Example 3: Efficacy Study of Anti-MRSA Composition A on Animal Model

Efficacy study on the composition A was conducted in C57bl-6 Mice and Sprague Dawley rats.

3a: Methicillin-Resistant *S. aureus* (MRSA) Intra-Venous Administration in Mice (25 Mice C57BL/6):

A suitable infectious dose of $2.4 \times 10^7$ CFU/ml was provided by 0.1 mL of bacterial stock injected intravenously in each mouse. Oral or IP administration of the composition A occurred 15 minutes after injection of the bacteria and once daily for a further five days.

Five groups of five C57BL/6 Mice each were used and the groups and treatment dosage dose were as shown in Table 5:

TABLE 5

| Group mice | Treatment | Dosage | Dose Level | Dose Volume | Number of Animals |
|---|---|---|---|---|---|
| 1 | Control saline (oral gavage) | na | na | 400 ul/200 g | 5 |
| 2 | IP | 500 mg/kg | MTD | 10 ul/20 g | 10 |
| 3 | oral gavage | 2000 mg/kg | MTD | 40 ul/20 g | 10 | na = not applicable

Results

Control Group 1: All 5 mice from the control group died consecutively on days 5, 6, and 7 from bacterial infections. One day prior to death, there were observations of sickness, including apatia, restriction of movement, and loss of appetite. They were found dead overnight. Histological changes could not be observed from the carcasses.

IP Group 2: In the itraperitoneal group, two of ten mice (20%) died on the third day of the study after the third injection of High Dose (LD50) 500 mg/kg Composition A. The cause of death was not confirmed. The remainder of the mice (80%) survived post day 5 including MRSA administration with no apparent sickness.

Gavage Group 3: In the gavage group, two of ten mice (20%) died; one each on days 3 and 7. The remainder of the mice (80%) survived post day 5 including MRSA administration with no apparent sickness.

3b: (MRSA) Intra-Venous (Tail Vein) Administration in Mice (25 Mice C57BL/6)

Mice were inoculated intravenously with $1 \times 10^7$ CFU/ml of MRSA. The test composition was administered to the inoculated mice by oral gavage. At the end of study, post 14 days, blood was collected and cultured for bacteria detection.

Five groups of five C57BL/6 Mice each were used and the groups were as follows:

1) 5 mice (G1) control (only MRSA)
2) 5 mice (G2) treatment 500 mg/kg of Composition A, once/day for 14 days IV induction of MRSA
3) 5 mice (G3) treatment 100 mg/kg of Composition A, once/day for 14 days IV induction of MRSA
4) 5 mice (G4) treatment 50 mg/kg of Composition A, once/day for 14 days IV induction of MRSA
5) 5 mice (G5) treatment 25 mg/kg of Composition A, once/day for 14 days IV induction of MRSA Results With the exception of Group 1 all blood cultures from all dosed treatment animals did not show any bacterial growth. In the control group G1, mouse no. 5 died on day 10, post IV administration of *Staphylococcus aureus*. All the rest of the animals (four animals) showed massive bacterial growth. The health of the animals in the treatment groups was not affected.

4b: Rat Full-Thickness Excision Model on Sprague-Dawley Rats.

Procedure (Summary):

a) Wound sites were prepared on the back of each anesthetized rat by exposing ~2 cm² of fascia.

b) The exposed fascia was inoculated with a 100-µL suspension of $10^7$ CFU/mL of ATCC USA300 *S. aureus*.

c) After 15 minutes, the wounds were treated with 0.4 ml of Composition A or with sterile saline (recovery controls) and repeated daily for 5 consecutive days. Five days following treatment, a swab was taken from the wound and cultured on tryptic soy agar, incubated overnight at 35° C., and colonies were counted to determine organism survival.

d) Three groups of three adult male rats each were used and the groups were as follows:

Groups:

Total animals: 9 rats received topical or oral (gavage) administration of test composition or saline control once daily for 5 days.

Group 1) 3 rats (control) received saline (400 uL/200 g rat); topical, 1× daily for 5 days Group 2) 3 rats treated with 2000 mg/kg Composition A (400 uL/200 g rat); topical 1× daily/5 days Group 3) 3 rats treated with 500 mg/kg Composition A (100 uL/200 g rat); oral administration 1× daily/5 days Group Assignments and Dose Levels

| Group rats | Treatment | Dosage | Dose Level | Dose Volume | Number of Animals |
|---|---|---|---|---|---|
| 1 | Rat wound topical application | 2000 mg/kg | ND | 400 uL/200 gr rat | 3 |
| 2 | Rat wound oral gavage | 500 mg/kg | ND | 100 uL/200 gr rat | 3 |
| 3 | Rat wound control | 2000 mg/kg (saline) | na | 400 uL/200 gr rat | 3 |

ND = not determined;
na = not applicable

Results
Control Group

All animals showed evidence for an active bacterial infection in the area of the wound. A thick yellow/green opaque liquid was produced in the infected tissue, consisting of dead white blood cells and bacteria with tissue debris and serum. This was observed in all 3 rats from control group. All animals survived.
Topical Group In the topical application group (see images in appendix for Group 2), there was a significant improvement in the appearance of the wound, showing no puss or any kind of secretion compared to the "no treatment" group (saline), where the wound showed infection. Slight necrosis was observed post day 5 in "treatment group" (topical application). This effect may be due to the test material (2000 mg/kg treatment with repeated 5 day administration). No signs of sickness were observe in the topical application group.
Gavage Group In the gavage group, all rats died on days 3, 4, and 5. The dose of 500 mg/kg may have produced the death of rats by the accumulation of the composition in repeated administration.
4b: Rat Full-Thickness Excision Model on Sprague-Dawley Rats.

Wound sites were prepared on the back of each anesthetized rat by exposing ~2 cm2 of fascia. Five adult male Sprague-Dawley rats, with one wound site each were used for each treatment group. The exposed fascia was inoculated with a 100-μL suspension of $1 \times 10^7$ CFU/mL of ATCC us, 300 *S. aureus*. After 15 minutes, the wounds were treated, via topical application, with 0.4 ml of Composition A or with sterile saline (recovery controls) and repeated daily for 14 consecutive days. Fourteen days following treatment, a swab taken from the wound was cultured on tryptic soy agar, incubated overnight at 35° C., and colonies were counted to determine organism survival.

Five groups of five Sprague-Dawley Rats each were used and the groups were as follows:
1) 5 Rats (G1) control (only MRSA)
2) 5 Rats (G2) treatment 25 mg/kg of Composition A, once/day for 14 days direct wound application induction of MRSA
3) 5 Rats (G3) treatment 50 mg/kg of Composition A, once/day for 14 days direct wound application induction of MRSA
4) 5 Rats (G4) treatment 100 mg/kg of Composition A, once/day for 14 days direct wound application induction of MRSA
5) 5 Rats (G5) treatment 500 mg/kg of Composition A, once/day for 14 days direct wound application induction of MRSA At the end, post 14 days, a swab from wound was collected and cultured for bacteria detection.
Results In Group 1, multiple colonies were present in all five blood cell culture agar plates from all five rats. In Group 2, the blood agar culture presents two small colonies from rat no. 7, and rat no. 9. In Group 3, the blood agar culture plates showed presence of four small colonies from rat nos. 12 to 14. In Group 1, zero colonies were observed in the blood agar culture plates.

All groups with treated wounds show no sign of infection. All wounds were 100% healed. In the control group the wound was infected.

Example 5: Oral Dose and Topical Application Toxicity Study

Repeated dose oral toxicity and topical application toxicity study was conducted in BALB/C mice to ascertain the safety of Composition A following repeated oral or topical administration.
5a: Two Weeks Repeated Dose Oral Toxicity Study
Procedure Composition A was administered to BALB/C mice (n=5 males and 5 females per group) daily by oral gavage at doses of 0 mg/kg/day (40 μl/20 g olive oil), 1000 mg/kg/day (40 μl/20 g composition A), 300 mg/kg/day (40 μl/20 g composition A), and 100 mg/kg/day (40 μl/20 g composition A) for 14 days.

During the dosing period, the animals were observed daily immediately after administration and again 6 hours post administration for clinical signs of toxicity.

Animals that died or were terminated in a moribund state during the test period were necropsied, the organs weighed, and collected for histopathological analysis. Surviving animals were terminated 24 hours after the necropsied, the organs weighed, and fixed for histopathological analysis.

Blood and urine was collected and analyzed from each animal at time 0 (pre-dose), Day 1 (24 hrs.), Day 7, and Day 14 (end of study) for hematology, CBC, blood chemistry and urinalysis.
Results Oral administration of the test composition at doses up to 1000 mg/kg/day showed no effect on body weight or body weight gain in either male or female mice.

Hematology-Some significantly different numbers at any dose are not drug related.

Clinical Chemistry—There was no drug effect at any dose
Urine Analysis—There was no drug effect at any dose or time point Gross Pathology—We concluded that the observed differences were not related to the test composition Histopathology—
Some findings or incidental findings were not related to composition A at any doses.

Throughout the study duration of 14 days, no sickness was observed in the mice.

The above results confirmed that oral administration of Composition A in a high dose (1000 mg/kg) did not produce any adverse effect.
5b: Two Weeks Repeated Dose Topical Application Toxicity Study
Procedure Composition A was administered to BALB/c mice (n=5 males and 5 females per group) daily by topical application at doses of 0 mg/kg/day (40 μL/20 g olive oil), 1000 mg/kg/day (40 µL/20 g composition A), 300 mg/kg/day (40 µL/20 g composition A), and 100 mg/kg/day (40 µL/20 g composition A) for 14 days.

Each mouse was placed under isofluorane gas anesthesia; on the back of the shoulder, the fur was clipped and a 3-4 mm circular section of skin was removed creating an artificial wound. The composition was applied daily for 14 days over the created wound. The wound area was measured on day 0, day 7, and day 14.

During the dosing period, the animals were observed daily immediately after administration and again 6 hours post administration for clinical signs of toxicity.

Animals that died or were terminated in a moribund state during the test period were necropsied, the organs weighed, and collected for histopathological analysis. Surviving animals were terminated 24 hours after the last dose, necropsied, the organs weighed, and fixed for histopathological analysis.

Blood and urine was collected and analyzed from each animal at time 0 (pre-dose), Day 1 (24 hrs.), Day 7, and Day 14 (end of study) for hematology, CBC, blood chemistry and urinalysis.

Results

Topical administration of the test composition at doses up to (1000 mg/kg) showed no effect on body weight or body weight gain in both male and female mice.

Hematology—Some significantly different numbers at any dose are not drug related.

Clinical Chemistry—There was no drug effect at any dose.

Urine Analysis—There was no drug effect at any dose or time point.

Gross Pathology—We concluded that the observed differences were not related to the test composition.

Histopathology—Some findings or incidental findings were not related to composition A at any doses.

Throughout the study duration of 14 days, no sickness in the mice was observed The above results confirmed that topical application of Composition A in a high dose (1000 mg/kg) did not produce any adverse effect.

Example 6: Toxicokinetics Study for Oral Dose and Topical Application Toxicity

Toxicokinetics study for two weeks repeat dose oral toxicity and topical application toxicity of anti-bacterial Composition A was conducted in BALB/C mice to determine the amount/level of undecylenic acid analyte from Composition A in K2EDTA plasma samples in mice at different time points following the administration.

An LC/MS/MS procedure (M150911) was developed for the quantification of undecylenic acid in mouse K2EDTA plasma. Undecylenic acid and the internal standard (9-Decenoic acid) were isolated from mouse K2EDTA plasma by liquid-liquid extraction (MTBE was used as solvent). The extracted samples were transferred to clean injection vials. A 5 µL sample was injected into the LC/MS/MS system for analysis. The standard curve range was 0.5-100 µg/mL of undecylenic acid in K2EDTA plasma. A 50 µL K2EDTA plasma sample aliquot was used for sample preparation and analysis. All study samples were within the stability parameters established during validation of the method. The stability parameters include reinjection stability of extracted samples for up to 29.8 hours on autosampler at 15° C.; refrigeration stability of extracted samples for up to 69.4 hours at 2-8° C.; bench-top stability of unextracted samples for up to 5.5 hours; and freeze-thaw stability for up to four freeze-thaw cycles, and long-term storage stability of the QC samples for up to 25 days at −70° C. (long enough to cover the study sample storage period).

Each analytical batch contained one set of calibration standards placed at the beginning of the run. The peak areas for undecylenic acid and the internal standard were determined using the Analyst software. A quadratic regression (weighted 1/×2) was applied to a plot of the peak area ratio versus concentration for the standards to obtain the calibration curve. The sample concentrations are calculated from the curve parameters as performed by the Analyst software version 1.4.2.

6a: Toxicokinetics for Oral Dose

Procedure

Composition A was administered to BALB/C mice (n=18 males and 18 females per group) by oral gavage at doses of 0 mg/kg/day (40 µl olive oil), 1000 mg/kg/day (40 µl composition A), 300 mg/kg/day (40 µl composition A), and 100 mg/kg/day (40 µl composition A) and serial blood samples were taken from six mice per time point (3, 6, 8, 12, and 24 hours) on Day 1 and Day 14 of administration.

1. Group 1 Control—time 0. Blood samples were collected from six mice (3 males and 3 females).
2. Group 2 High Dose—1000 mg/kg—time 3, 6, 8, 12, and 24 hours on Day 1 and Day 14 of administration. Blood samples from six mice (3 males and 3 females) were collected at each time point.
3. Group 3 Medium Dose—300 mg/kg—time 3, 6, 8, 12, and 24 hours on Day 1 and Day 14 of administration. Blood samples from six mice (3 males and 3 females) were collected at each time point.
4. Group 4 Low Dose—100 mg/kg—time 3, 6, 8, 12, and 24 hours on Day 1 and Day 14 of administration. Blood samples from six mice (3 males and 3 females) were collected at each time point.

Blood was collected by cardiac puncture (approx. 500 µL), centrifuged, the plasma collected and pooled at each time point, then frozen at −80 C for future analysis.

Results

Oral administration of the test composition at a dose of 100 mg/kg resulted in no detectable analyte in the plasma of male mice 3 hours after administration. In female mice, one animal showed detectable levels of the test composition at this same dose level.

Oral administration of the test composition at a dose of 300 mg/kg resulted in detectable levels in the serum of both male and female mice three hours after administration. Serum plasma analyte concentrations at the 3 hour time point was less than 3 times higher than the serum analyte level seen in the one female mouse at the low dose (1.56 vs 2.35 ug/mL). By six hours after administration, only two of three males or females had detectable serum analyte levels while at 8 hours post dose, no males and one female had detectable analyte plasma levels. Interestingly, one male also showed detectable analyte levels at 24 hours at levels similar to that seen at 6 hours, however, serum samples collected at 8 and 12 hours showed no detectable analyte levels.

Oral administration of the test composition at the highest dose level (1000 mg/kg/day) resulted in detectable analyte levels in the serum in two of three males and all three females. Analyte levels between these five animals were variable ranging from 0.66 to 6.57 ug/ml. However, the highest value observed, 6.57 ug/mL was approximately 3 times greater than the highest serum analyte level seen at the 300 mg/kg/day dose level sample. Sequential serum samples with detectable analyte were present in two of the six animals tested. Of the six animals tested, only one had three sequential serum samples with measurable analyte levels.

Consequently, no AUC determinations could be performed. In addition, due to the limited number of animals and the variable nature of the values obtained, Cmax values are also not reliably determinable.

6b: Toxicokinetics for Topical Application

Procedure

Composition A was administered to BALB/C mice (n=18 males and 18 females per group) by topical application at doses of 0 mg/kg/day (40 µl olive oil), 1000 mg/kg/day (40 µl composition A), 300 mg/kg/day (40 µl composition A), and 100 mg/kg/day (40 µl composition A) and serial blood samples were taken from six mice per time point (3, 6, 8, 12, and 24 hours) on Day 1 and Day 14 of administration.

1. Group 1 Control—time 0. Blood samples were collected from six mice (3 males and 3 females).
2. Group 2 High Dose—1000 mg/kg—time 3, 6, 8, 12, and 24 hours on Day 1 and Day 14 of administration. Blood samples from six mice (3 males and 3 females) were collected at each time point.
3. Group 3 Medium Dose—300 mg/kg—time 3, 6, 8, 12, and 24 hours on Day 1 and Day 14 of administration. Blood samples from six mice (3 males and 3 females) were collected at each time point.
4. Group 4 Low Dose—100 mg/kg—time 3, 6, 8, 12, and 24 hours on Day 1 and Day 14 of administration. Blood samples from six mice (3 males and 3 females) were collected at each time point. Blood was collected by cardiac puncture (approx. 500 µL), centrifuged, the plasma collected and pooled at each time point, then frozen at −80 C for future analysis.

Results

Application of test composition topically at a dose of 100 ug/kg/day resulted in no detectable serum analyte levels in either male or female mice. At the 300 mg/kg/day dose level, serum analyte levels were below the level of detection in the male mice. In the female mice, at the 3 hour time point, two animals had detectable serum analyte levels. As these values were approximately half of what was observed in female mice orally administered the composition, it is possible that the serum analyte levels were secondary to grooming. Further support for this hypothesis comes from the one male animal with detectable serum analyte levels 3 hours after topical administration. In this case, the mouse had serum analyte levels that were comparable to that seen with oral administration. Based on these data, it is possible that the test composition is absorbed through the skin but it is equally likely that the serum analyte levels seen following topical administration at the middle dose are the result of the animals grooming.

At the 1000 mg/kg/day dose level, two males and two females had detectable serum analyte levels 3 hours post application. The serum analyte levels were lower than that seen following topical administration at the 300 mg/kg/day dose providing further support for oral uptake secondary to grooming.

The results from toxicokinetics studies suggest that absorption either by the oral or topical route appears to be limited. As a result, systemic exposures are also limited.

Example 7: Comparative Efficacy Study

Efficacy Study in comparison to leading anti-MRSA antibiotics was conducted in BALB/C mice.

7a. Administration Route: Oral Gavage 1) vancomycin

Group 1 (6 mice males)—MRSA Induction IP no treatment
Group 2 (6 mice males)—MRSA Induction IP— oral treatment for 7 days
Group 3 (6 mice males)—No Induction—oral treatment for 7 days
Group 4 (6 mice males)—MRSA Induction IP-oral treatment with composition A 2) clindamycine
Group 1 (6 mice males)—MRSA Induction IP no treatment
Group 2 (6 mice males)—MRSA Induction IP— oral treatment for 7 days
Group 3 (6 mice males)—No Induction—oral treatment for 7 days
Group 4 (6 mice males)—MRSA INDUCTION IP-oral treatment with composition A 3) erythromycine
Group 1 (6 mice males)—MRSA Induction IP no treatment
Group 2 (6 mice males)—MRSA Induction IP— oral treatment for 7 days
Group 3 (6 mice males)—No Induction—oral treatment for 7 days
Group 4 (6 mice males)—MRSA Induction IP-oral treatment with composition A 7b. Administration Route: Topical Application 1) bactroban Group 1 (6 mice males)—MRSA Induction (wound application) no treatment
Group 2 (6 mice males)—MRSA Induction (wound application)—treatment for 7 days
Group 3 (6 mice males)—No Induction—topical application treatment for 7 days
Group 4 (6 mice males)—MRSA Induction (wound application)—treatment with composition A Dosage for Comparative Test For Composition A Dose was 100 mg/kg. For the antibiotics the dose was as per RX prescription converted to mice Body Weights.

1-Erythromycin 250 mg/pt b.i.d. equals 2.1 mg/20 g mouse/day 300 mg total/12 mice Erythromycin 500 mg/pt b.i.d. equals 4.2 mg/20 g mouse/day 2-Clindamycin 150 mg/pt b.i.d. equals 1.25 mg/20 g mouse/day 200 mg total/12 mice Clincamycin 300 mg/pt b.i.d. equals 2.5 mg/20 g mouse/day 3-Vancomycine 250 mg/pt b.i.d. equals 2.1 mg/20 g mouse/day 300 mg total/12 mice 4-A small amount (0.1 g) of Bactroban Ointment was applied to the affected area/20 g mice/day.

Results

Blood Cell Culture Results for the Comparative Tests are as Discussed Below:

1. Vancomycin Group

Group 1—MRSA induction—No treatment: There was bacteria development from the blood taken from mice no. 1, 4, 5, 6.

Group 2—MRSA induction vancomycin treatment: There was bacterial growth one colony from animal no. 4 blood culture.

Group 3—NO MRSA induction vancomycin treatment; all probes negative.

Group 4—MRSA induction Composition A treatment: Negative.

The comparison between the treatments shows a slight advantage for the Composition A treatment, where no bacteria was found versus the vancomycin treatment that shows one colony.

2. Erythromycin Group

Group 1—MRSA induction No treatment: All six animals have positive colonies.

Group 2—MRSA induction; Erythromycin treatment: show two colonies in mice nr.1 and nr.2.

Group 3—No MRSA treatment with erythromycin: all probes negative but the pictures show some light reflection between probes 3 and 4, and, 5 and 6.

Group 4—MRSA induction with treatment with composition A: All probes negative—pictures show some light reflections.

The comparison between the treatment show a definite superior results in the groups treated with Composition A (negative results) and erythromycin that presents 2 positive colonies.

3. Clindamycin Group

Group 1—MRSA induction—No treatment: All samples show positive colonies.

Group 2—MRSA induction—Clindamycin treatment: All samples show negative colonies (light reflection effect at probe 1, 5 and 6).

Group 3—No MRSA—Clindamycin treatment: All negative (light effects at samples 1, 2, 3 and 6).

Group 4—MRSA induction Treatment with Composition A: All samples negative, light effects at no. 6 and no. 2.

The comparison between the treatment with Clindamycin and Composition A show both a positive effect.

4. Bactroban Group—Topical Application

Group 1—MRSA induction—no treatment: all samples show positive colonies.

Group 2—MRSA induction—Bactroban treatment: Blood probes negative, wound swab positive in mouse nr. 4, (5 colonies).

Group 3—no MRSA induction—Bactroban treatment: all negative.

Group 4—MRSA induction—Composition A treatment: blood probes negative, one probe positive from swab in animal nr. 2, (1 colony).

Comparison between Bactroban and Composition A topical application show a slight advantage for Composition A (five colonies in Bactroban and one colony in Composition A).

In addition Composition A presents the advantage that it spreads and diffuses all over the infected wound areas without touching the contaminated area, and can be applied by droplets versus Bactroban that needs to be applied in direct contact with the wound on the contaminated area. The Composition A used had the lowest concentration of 100 mg/kg.

Example 7: OECD Bovine Corneal Opacity and Permeability Test (BCOP)

Composition A was tested for potential ocular irritation using an alternative to the Draize methodology. This protocol is based on the methodology described in the current OECD Guideline for the Testing of Chemicals #437.

Method:

Three bovine corneas per group were dosed with 0.75 ml of composition A, Minimal Essential Media (MEM) (negative control), or 100% Ethanol (positive control). Following a 10-minute exposure for each group of dosed corneas, opacity measurements and sodium fluorescein permeability were determined. The results are summarized in Table 6:

TABLE 6

| Treatment | In Vitro Irritation Score (IVIS) | Corrected Mean Opacity Score | Corrected Mean Optical Density |
|---|---|---|---|
| composition A | 0.50 | 0.33 | 0.011 |
| MEM (negative control) | 0.76 | 0.67 | 0.006* |
| 100% Ethanol (positive control) | 32.34 | 22.66 | 0.645 |

Based on an In Vitro Irritation Score of less than 3, in accordance with EURL DB-ALM protocol No. 127, Composition A was considered to be non-irritant.

Example 8: 3T3 Neutral Red Uptake Phototoxicity Assay

The cytotoxicity and phototoxicity of the test composition to 3T3 cells (in the presence or absence of UVA light) was assessed by Neutral Red Uptake. The 3T3 Neutral Red Uptake Phototoxicity Assay (3T3 NRU PT), based on the OECD Guideline for Testing of Chemicals: No. 432, was designed to detect the phototoxicity induced by the combined action of a test composition and solar-simulated UVA+visible light in an in vitro cytotoxicity assay using the BALB/C 3T3 mouse fibroblast cell line as the test system.

The assay identifies aqueous-soluble compounds (or formulations) that have the potential to exhibit in vivo phototoxicity after systemic application.

An Ultraviolet-Visible light (UV-VIS) spectral scan was performed on a solution containing 0.1% of the test composition in a solution of 1% DMSO/HBSS. The scan showed that most of the absorbance occurred below the Ultraviolet A (UVA) and Ultraviolet B (UVB) regions (OD280 to OD400) and should not have any impact on the results of the 3T3 assay. For both the range-finding screen and the definitive test of the 3T3 assay, BALB/C 3T3 cells were seeded in the central 60 wells of duplicate 96-well microplates and maintained in culture for approximately 24 hours. The two 96-well plates were then preincubated with eight different concentrations of the test composition for approximately one hour. After preincubation, one plate was irradiated with a dose of 5 J/cm$^2$ Solar Simulated Light (SSL, containing wavelengths in the UVA and visible regions with >99% of UVB blocked out), while the duplicate plate was kept in the dark (No SSL). After UV irradiation, the treatment medium was replaced with culture medium and, after approximately 24 hours, cell viability was determined by neutral red uptake for three hours.

A range finding screen was performed to determine the acceptable concentrations for the definitive test. MS Excel® was used to calculate the EC50 values and Photo-Irritant Factor (PIF) for the test article and the Chlorpromazine (CPZ) positive control in both the Screen and the Definitive test. Results of the definitive test are summarized in Table 6:

TABLE 6

| Test Composition | Concentration Range Tested | EC50 No SSL | EC50 +SSL | PIF |
|---|---|---|---|---|
| composition A | 0.0068-0.1% | >0.1% | >0.1% | None |
| CPZ Positive Control | No SSL: 6.81-100 µg/ml +SSL: 0.22-3.16 µg/ml | 18.8 µg/ml | 0.4 µg/ml | 47.0 |

Test Composition A had EC50 values of >0.1% for both No SSL and +SSL; therefore, the Photo-Irritancy Factor (PIF) could not be calculated. This test composition therefore is not considered to have phototoxic potential in the 3T3 Neutral Red Uptake Phototoxicity Test.

Example 9: MatTek EpiDerm™ Skin Irritation Test (SIT)

This test was conducted to predict dermal irritation potential of test articles in the context of identification and classification of skin irritation hazard according to the European Union (EU) classification (R38 or no label), United Nations Globally Harmonized System of Classification and Labeling of Chemicals (GHS) classification system (Category 2 and non-irritants), and OECD Guideline for the Testing of Chemicals No. 439—In Vitro Skin Irritation: Reconstructed Human Epidermis Test Method. This study was designed based on MatTek protocol in vitro EpiDerm™ Skin Irritation Test.

MatTek EpiDerm™ tissue samples were treated in triplicate with the test composition, Negative Control and Positive Control for 60 minutes. Following treatment and subsequent incubation time, the viability of the tissues was determined using Methyl thiazole tetrazolium (MTT) uptake and reduction. The absorbance of each sample was measured at 540 nm. The viability was then expressed as a percent of control values. If the mean tissue viability was <50%, the test material was classified as an irritant; if the mean tissue viability was >50%, the test material was classified as a non-irritant. The results are summarized in table 7:

TABLE 7

| Test and Control Article Identity | Mean Tissue Viability | Irritancy Classification |
| --- | --- | --- |
| Composition A | 106.7% | Non-Irritant |
| Phosphate Buffered Saline (Negative Control) | 100.0% | Non-Irritant |
| 5% Sodium Dodecyl Sulfate (Positive Control) | 3.1% | Irritant |

Example 10: Preservative Challenge Test

The USP-NF<51>—Preservative Challenge Test was conducted to evaluate the antimicrobial activity of the test composition for use in cosmetics and personal care products.

TABLE 8

Results of Challenge tests analysis

| Micro-organism | Initial inoculums | 10 minutes after innoculation | 7 days after |
| --- | --- | --- | --- |
| Staphylococcus aureus (cfu/g) | $1.6 \times 10^4$ | <10 | |
| Staphylococcus aureus (cfu/g) | $7.3 \times 10^5$ | <10 | <10 |
| E. coli (cfu/g) | $4.4 \times 105$ | <10 | <10 |
| Pseudomonas aeruginosa (cfu/g) | $3.5 \times 105$ | <10 | <10 |
| Candida albicans (cfu/g) | $3.6 \times 105$ | <10 | <10 |
| Aspergillus niger (cfu/g) | $6.2 \times 105$ | <10 | <10 |

Example 11: Evaluation Antimicrobial Activity of a Known Tegaderm and Effect of Composition a The cellulose part of Tegaderm 3584 from 3M was tested for antimicrobial activity, which did not show any antimicrobial activity against various bacterial species. Introduction of 5 mg of composition A to 3M cellulose fibre (500 mg) of Tegaderm, resulted in elimination of 99.99% of wide range of bacteria including E. Coli.

Example 12: Evaluation of Antimicrobial Activity of Composition a Incorporated Paper Product Via Dilution Test a) 200 microliter of E. coli B was grown in 10 ml of TSB medium overnight. Serial dilution test showed high E. coli activity (108 CFU/mL) in petri dish. 200 µL of E. coli B and 200 µL of composition A were dispersed in 10 ml of TSB medium overnight. Serial dilution test showed no E. coli activity, concluding that incorporation of composition A resulted in 99.999% E. coli B and bacteriophage resistance E. coli B.
b) 0.4 g spruce/pine/fir (SPF) pulp paper sheet patch containing 200 µL of composition A was immersed in 10 mL TSB medium containing 200 µL E. coli. Serial dilution test showed no E. Coli activity.
c) 0.4 g SPF paper sheet patch containing 200 µL of composition A was immersed in 10 mL overnight cultured E. coli (fully grown 108 CFU/mL). Serial dilution test showed four log of reduction in E. coli activity (correspond to 80% drop in E. coli activity.

Example 13: Evaluation of Antimicrobial Activity of Composition a Incorporated Plastic Product Via Serial Dilution Test 1.0 g of polyethylene (PE, melting 90-100° C., Mw of 4000) was heated to melt (110° C.), then 500 µl of Composition A was added to PE melt solution. The mixture was placed in flat petri dish to reach room temperature and solidified to film. About 0.5 g of sample (PE-composition A) was immersed in E. coli suspension overnight at 37° C. Complete E. coli removal was observed after serial dilution test (108 CFU/mL to Zero).

DSC analysis showed that composition A and PE are not miscible blend and as a result a complete diffusion release of composition A was confirmed. Physical structure property of PE should remain same (further DMA analysis is required to confirm it.) SEM analysis of PE/composition A showed that composition A is uniformly embedded through PE film.

Same results were obtained when composition A was mixed with PE having MW of about 125 k and 100K (complete removal of E. coli).

The invention claimed is:
1. An antibacterial composition comprising:
a) about 50% to about 70% of an unsaturated fatty acid or a pharmaceutically acceptable salt thereof, by weight of the total weight of the composition, wherein the unsaturated fatty acid is undecylenic acid;
b) about 20% to about 30% of lactic acid or a pharmaceutically acceptable salt thereof, by weight of the total weight of the composition;
c) about 10% to about 15% of at least one amino alcohol.

2. The antibacterial composition according to claim 1, wherein the amino alcohol has a formula:

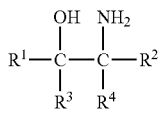

wherein $R^1$ and $R^3$ are each independently H or C1-C6alkyl, $R^2$ and $R^4$ are each independently H or C1-C6alkyl, or $R^2$ is C1-C6 and $R^4$ is $CH_2OH$.

3. The antibacterial composition according to claim 2, wherein the composition is suspended or dispersed in water.

4. The antibacterial composition according to claim 1, wherein the amino alcohol is 2-amino-2-methyl-1-propanol (AMP).

5. The antibacterial composition according to claim 4, wherein the composition is suspended or dispersed in water.

6. The antibacterial composition according to claim 1, wherein the amino alcohol is 2-amino-2-ethyl-1,3-propanediol.

7. The antibacterial composition according to claim 6, wherein the composition is suspended or dispersed in water.

8. The antibacterial composition according to claim 1, wherein the amino alcohol is ethanol amine.

9. The antibacterial composition according to claim 8, wherein the composition is suspended or dispersed in water.

10. The antibacterial composition according to claim 1:
wherein undecylenic acid is about 55% to about 60%;
lactic acid is about 25% to about 30%.

11. The antibacterial composition according to claim 1, comprising;
about 58% of undecylenic acid acid;
about 28% of lactic acid; and
about 14% the amino alcohol.

12. The antibacterial composition according to claim 11, wherein the composition is suspended or dispersed in water.

13. A pharmaceutical formulation comprising a composition as defined in claim 1, and a pharmaceutically acceptable carrier.

14. The pharmaceutical formulation according to claim 13, where said formulation is for topical administration.

15. The pharmaceutical formulation according to claim 14, where said formulation is in the form of a cream, lotion or a gel.

16. The pharmaceutical formulation according to claim 13, where said formulation is for oral administration.

17. A method of killing and/or inhibiting the growth of bacteria on a substrate comprising applying an effective amount of the antibacterial composition as defined in claim 1.

18. The method of claim 17, wherein said antibacterial composition is used in combination with one or more anti-microbial agent(s).

19. A transdermal patch comprising the antibacterial composition as defined in claim 1.

20. A personal care product comprising the antibacterial composition as defined in claim 1.

21. The personal care product of claim 20, wherein said personal care product is a cosmetic product, soap, deodorant, shampoo, mouthwash or toothpaste.

22. A household product comprising the antibacterial composition as defined in claim 1.

23. The household product of claim 22, wherein said household product is a cleanser, polish, paint, spray, soap, or detergent.

24. A paper product comprising the antibacterial composition as defined in claim 1.

25. A plastic product comprising the antibacterial composition as defined in claim 1.

26. The composition of claim 1, further comprising one or more of a carrier, diluent, excipient, flavouring agent, solubilizer, lubricant, suspending agent, and binder.

27. The antibacterial composition according to claim 1, wherein the composition is suspended or dispersed in water.

* * * * *